(12) United States Patent
Alanine et al.

(10) Patent No.: US 6,407,235 B1
(45) Date of Patent: Jun. 18, 2002

(54) PRODRUG ACID ESTERS OF [2-(4-BENZYL-3-HYDROXY-PIPERIDIN-1-YL)-ETHANSULFONYL]PHENOL

(75) Inventors: Alexander Alanine, Schlierbach (FR); Bernd Buettelmann, Schopfheim (DE); Holger Fischer, Grellingen (CH); Marie-Paule Heitz Neidhart, Hagenthal le Bas (FR); Joerg Huwyler, Burg; Georg Jaeschke, Basel, both of (CH); Emmanuel Pinard, Linsdorf (FR); René Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/931,431

(22) Filed: Aug. 16, 2001

(51) Int. Cl.[7] ............. C07D 211/42; C07D 403/12; C07D 413/12

(52) U.S. Cl. ............. 544/130; 544/360; 546/24; 546/221

(58) Field of Search ............. 544/130, 360; 546/24, 221

(56) References Cited

FOREIGN PATENT DOCUMENTS

| EP | 824 098 | 2/1998 |
|----|---------|--------|
| WO | 95/25721 | 9/1995 |
| WO | 00/75109 | 12/2000 |

OTHER PUBLICATIONS

Bundgaard, *Drugs of the Future,* vol. 16(5), pp. 443–458 (1991).

*Primary Examiner*—Robert W. Ramsuer
(74) *Attorney, Agent, or Firm*—George W. Johnston; Patricia S. Rocha-Tramaloni; Arthur D. Dawson

(57) ABSTRACT

The invention is a compound of the formula

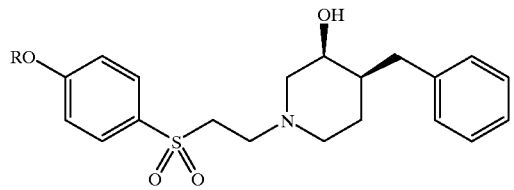

I wherein
R is
a) $-C(O)(CH_2)_nC(O)OH$,
b)

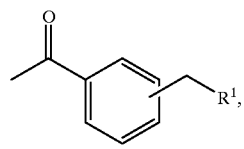

wherein $R^1$ is $-N(R^2)(R^3)$, or is a five or six member aromatic or non-aromatic heterocyclic ring having one or more heteroatoms selected from nitrogen, oxygen or sulfur, unsubstituted or substituted by lower alkyl,
c) $-P(O)(OH)_2$, or is
d) $-C(O)(CH_2)_nNHC(O)(CH_2)_nN(R^2)(R^3)$; and
$R^2/R^3$ are hydrogen or lower alkyl;
n is 1, 2, 3 or 4;
or a pharmaceutically acceptable acid addition salt thereof

18 Claims, No Drawings

PRODRUG ACID ESTERS OF [2-(4-BENZYL-3-HYDROXY-PIPERIDIN-1-YL)-ETHANSULFONYL]PHENOL

FIELD OF INVENTION

The present invention is generally related to acid esters of [2-(4-benzyl-3-hydroxy-piperidin-1-yl)-ethansulfonyl] phenol, and more particularly to acid esters that enhance the solubility of the parent compound and are hydrolyzed under in vivo conditions thus serving as prodrugs for the parent compound.

BACKGROUND

A prodrug is in most cases a pharmacologically inactive derivative of a parent drug molecule that requires spontaneous or enzymatic transformation within the body in order to release the active drug, and that has improved delivery properties over the parent drug molecule. It has been shown that a molecule with optimal structural configuration and physicochemical properties for eliciting the desired therapeutic response at its target site does not necessarily possess the best molecular form and properties for its delivery to its point of ultimate action. Usually, only a minor fraction of doses administered reaches the target area and since most agents interact with non-target sites as well, an inefficient delivery may result in undesirable side effects. This fact of differences in transport and in situ effect characteristics for many drug molecules is the basic reason why bioreversible chemical derivatization of drugs, i.e., prodrug formation is a means by which a substantial improvement in the overall efficacy of drugs can often be achieved.

Prodrugs are designed to overcome pharmaceutically and/or pharmacokinetically based problems associated with the parent drug molecule that would otherwise limit the clinical usefulness of the drug. The advantage of a prodrug lies in its physical properties, such as enhanced water solubility for parenteral administration at physiological pH compared to the parent drug, or it enhances absorption from the digestive tract, or it may enhance drug stability for long-term storage.

In recent years several types of bioreversible derivatives have been exploited for utilization in designing prodrugs. Using esters as a prodrug type for drugs containing carboxyl or hydroxyl fumction is most popular. Further well-known are prodrug derivatives of peptides, 4-imidazolidinones and the like, described in Drugs of the Future, 1991, 16(5), 443–458 or N-oxides, described for example in U.S. Pat. No. 5,691,336.

Compounds of formula

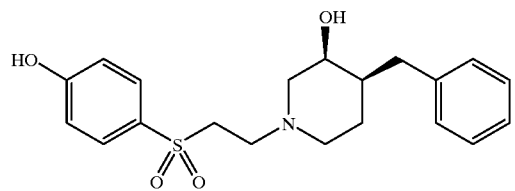

II are known as NMDA (N-methyl-D-aspartate)-receptor-subtype selective blockers. Compounds of formula II have limited water solubility at physiological pH, not allowing bolus injections. A similar compound of formula II is generically described in WO 95/25721, wherein the formula does not contain a hydroxy group on the piperidine ring. These compounds are described to possess activities on the glutamat receptor or AMPA receptor for the treatment of diseases which are related to these receptors.

Similar compounds are described in EP 824 098, in which the piperidine ring is substituted by a hydroxy group in 4-position. These compounds are described to possess activities on the NMDA receptor and are useful in the treatment of acute forms of neurodegeneration caused, for example, by stroke and brain trauma, and chronic forms of neurodegeneration such as Alzheimer's disease, Parkinson's disease, ALS (amyotrophic lateral sclerosis), neurodegeneration associated with bacterial or viral infections and acute/chronic pain. Furthermore, it is known from WO 00/75109, that the compound of formula II is a good NMDA receptor subtype specific blocker, neuroprotective in vivo and less active as blockers of the hERG potassium channels and thus is much less likely to have pro-arrhythmic activity in man.

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in diff rent brain areas. Heteromeric combinations of NR-1 members with different NR-2 subunits result in NMDA receptors, displaying different pharmacological properties. Possible therapeutic indications for NMDA receptor subtype specific blockers include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, diseases such as schizophrenia, anxiety and depression and acute/chronic pain.

SUMMARY

The present invention relates to a compound of the formula

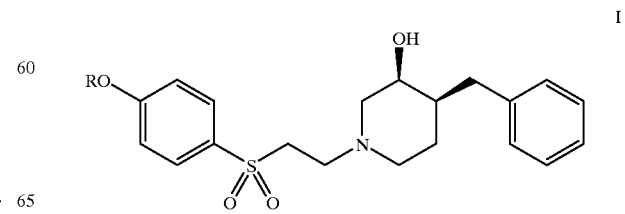

I wherein
R is
  a) —C(O)(CH₂)ₙC(O)OH,

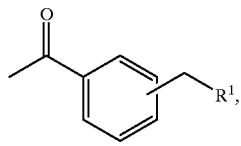

wherein R¹ is —N(R²)(R³) and R²/R³ are hydrogen or lower alkyl, or is a five or six member aromatic or non-aromatic heterocyclic ring containing one or more heteroatoms selected from nitrogen, sulfur or oxygen, unsubstituted or substituted by lower alkyl,
  c) —P(O)(OH)₂, or is
  d) —C(O)(CH₂)ₙNHC(O)(CH₂)ₙN(R²)(R³); and
n is 1, 2, 3 or 4;
or a pharmaceutically acceptable acid addition salt thereof.

It has been found that compounds of formula I may be used as prodrugs of compounds of formula

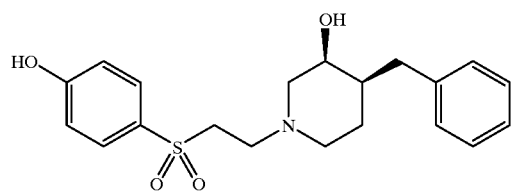

II which are NMDA (N-methyl-D-aspartate)-receptor-subtype selective blockers.

It has surprisingly been shown that the compounds of the invention of formula I fulfill all requirements of a good prodrug. Specifically, it has been shown that compounds of the invention have up to 10-fold higher solubility over the parent compound at physiological pH. Additionally the compounds of the invention have an unexpected stability in solution at room temperature up to 48 h but also demonstrate a fast hydrolysis in plasma.

The present invention is a novel compound of formula I, its use as a prodrug in the treatment or prophylaxis of diseases caused by overactivation of respective NMDA receptor subtypes, which include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and diseases such as schizophrenia, anxiety, depression and acute/chronic pain, the use of these compounds for manufacture of corresponding medicaments, processes for the manufacture of these novel compounds and medicaments, containing them.

The most preferred indication in accordance with the present invention is the treatment or prevention of stroke.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "five or six member aromatic or non-aromatic heterocyclic ring containing one or more hetero atoms selected from nitrogen, sulfur or oxygen, unsubstituted or substituted by lower alkyl" denotes, for example pyrrol-1-yl, imidazol-1-yl, piperidin-1-yl, piperazin-1-yl or morpholin-4-yl. Preferred are piperazin-1-yl or morpholin-4-yl. It is preferred that the heterocyclic rings contain one or two hetero atoms.

The term "physiological pH" means a pH of around 7, preferably about 7.4.

Exemplary preferred are compounds of formula 1, in which R is —C(O)(CH₂)ₙC(O)OH and n is 2, for example the following compound:

Succinic acid mono-{(3S,4S)-4-[2-(4-benzyl-3-hydroxy-piperidin-1-yl)-ethanesulfonyl]-phenyl}ester.

Further preferred are compounds of formula 1, in which R is

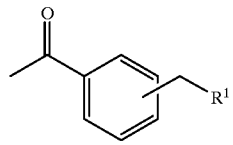

and R¹ is as above. Especially preferred are compounds wherein R¹ is morpholinyl, 4-methyl-piperazinyl or —N(R²)(R³) with R² and R³ as above.

Examples of such compounds when R¹ is morpholinyl are:

4-morpholin-4-ylmethyl-benzoic acid (3S,4S)-4-[2-(4-benzyl-3-hydroxy-piperidin-1-yl)-ethanesulfonyl]-phenyl ester; and 3-morpholin-4-ylmethyl-benzoic acid (3S,4S)-4-[2-(4-benzyl-3-hydroxy-piperidin-1-yl)-ethanesulfonyl]-phenyl ester.

Further preferred are compounds of formula 1, in which R is

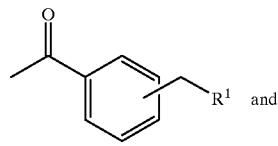 and

R¹ is 4-methyl-piperazinyl. Examples of such compounds are:

4-(4-methyl-piperazin-1-ylmethyl)-benzoic acid (3S,4S)-4-[2-(4-benzyl-3-hydroxy-piperidin-1-yl)-ethanesulfonyl]-phenyl ester, 3-(4-methyl-piperazin-1-ylmethyl)-benzoic acid (3S,4S)-4-[2-(4-benzyl-3-hydroxy-piperidin-1-yl)-ethanesulfonyl]-phenylester, Further preferred are compounds of formula 1, in which R is

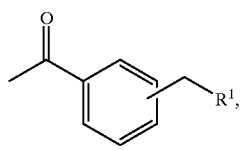

R[1] is —N(R[2])(R[3]) and R[2]/R[3] are hydrogen or lower alkyl. Examples of such compounds are:

- 4-aminomethyl-benzoic acid (3S,4S)-4-[2-(4-benzyl-3-hydroxy-piperidin-1-yl)-ethanesulfonyl]-phenyl ester;
- 3-methylaminomethyl-benzoic acid (3S,4S)-4-[2-(4-benzyl-3-hydroxy-piperidin-1-yl)-ethanesulfonyl]-phenyl ester; and
- 4-methylaminomethyl-benzoic acid (3S,4S)-4-[2-(4-benzyl-3-hydroxy-piperidin-1-yl)-ethanesulfonyl]-phenyl ester.

Exemplary preferred are further compounds of formula 1, in which R is —P(O)(OH)$_2$, for example the following compound:

- phosphoric acid mono-{(3S,4S)-4-[2-(4-benzyl-3-hydroxy-piperidin-1-yl)-ethanesulfonyl]-phenyl}ester.

Also preferred are further compounds of formula 1, in which R is —C(O)(CH$_2$)$_2$NHC(O)(CH$_2$)$_2$NH$_2$, which is

- 3-(3-amino-propionylamino)-propionic acid (3S,4S)-4-[2-(4-benzyl-3-hydroxy-piperidin-1-yl)-ethanesulfonyl]-phenyl ester.

The present compounds of formula I and their pharmaceutically acceptable salts can be prepared by methods known in the art, for example, by processes described below, which process comprises a) reacting a compound of formula

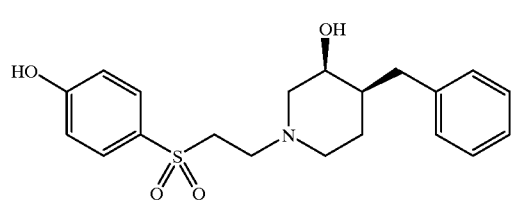

II with

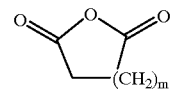

III to give a compound of formula

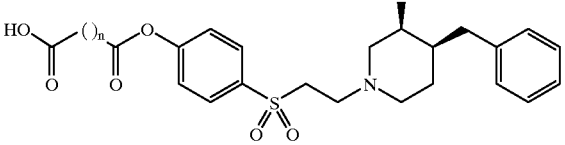

I-1 wherein m is 1–3 and n is 2–4, or b) reacting a compound of formula II with (BnO)$_2$P(H)O/CCl$_4$/DMAP/Hünigs base and hydrogenating the obtained compound to a compound of formula

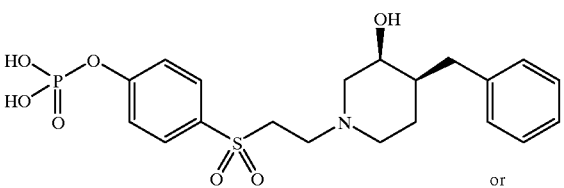

I-2 or reacting a compound of formula II with a compound of formula

HOOC—(CH$_2$)$_n$NHC(O)(CH$_2$)$_n$NH—Boc    IV, cleaving off the Boc group to give a compound of formula

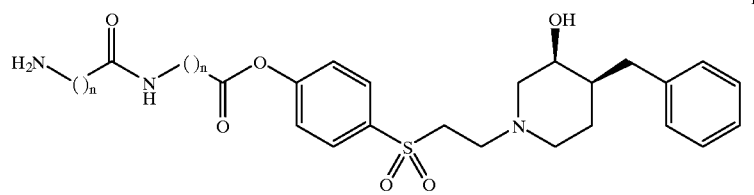

I-3 reacting a compound of formula II with a compound of formula

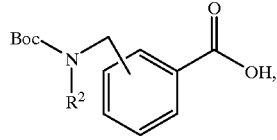

V cleaving off the Boc group with TFA (trifluoroacetic acid) to give a compound of formula

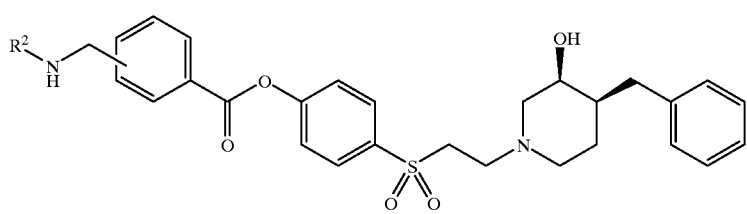

I-4 reacting a compound of formula

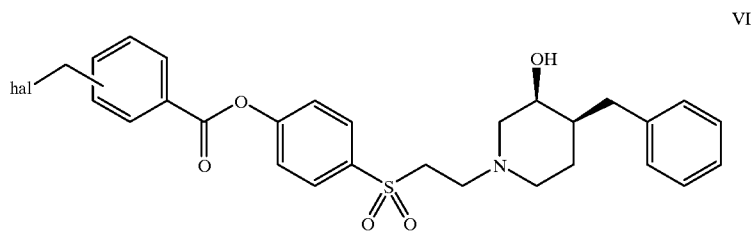

VI with morpholin or 4-methyl-piperazin to give a compound of formula

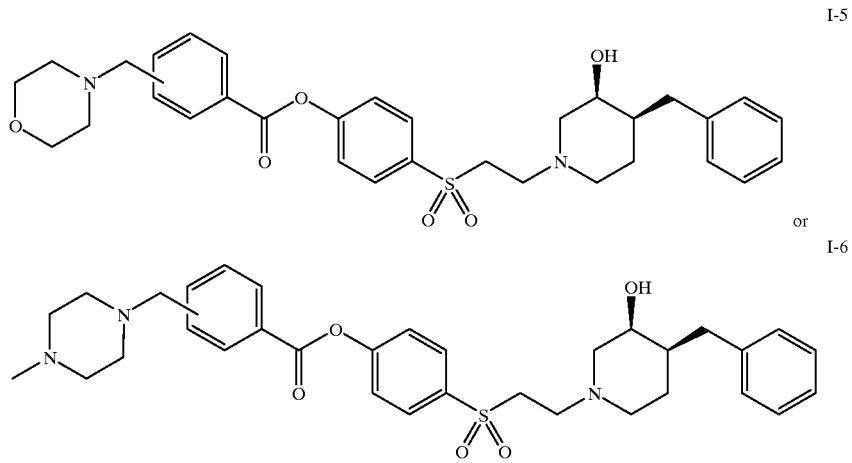

and
if desired, converting the compound obtained into a pharmaceutically acceptable acid addition salt.

In accordance with this procedure, a compound of formula I may be prepared, for example, in accordance with reaction variant a) as follows:

To a solution of the compound of formula II in a solvent, such as methylene chloride, is added succinic acid or an equivalent compound of formula III and DMAP (dimethylaminopyridine). The reaction mixture is refluxed some hours to obtain the desired compound of formula I-1.

In accordance with process variant b) a compound, described in example 11, for example phosphoric acid dibenzyl ester (3S,4S)-4-[2-(4-benzyl-3-hydroxy-piperidin-1-yl)-ethanesulfonyl]-phenyl ester is hydrogenated at room temperature in conventional manner to obtain a compound of formula I-2.

Process variant c) describes the process for preparation of a compound of formula I-3. The process is carried out by reacting the compound of formula II with a compound of formula IV, for example with 3-(3-tert-butoxycarbonylamino-propionylamino)-propionic acid, in the presence of DMAP (4-dimethylaminopyridine) and DAPEC (N-(3-dimethylaminopropyl)-n-ethylcarbodiimide hydrochloride) at a temperature of about 0° C. The reaction mixture is then treated with TFA (trifluoroacetic acid).

Furthermore, in accordance with reaction variant d) a compound of formula I-4 is obtained. The reaction is carried out by reaction of the compound of formula II with a compound of formula V, for example with 3-[(tert-butoxycarbonyl-methyl-amino)-methyl]benzoic acid, in the presence of DMAP (4-dimethylaminopyridine) and DAPEC (N-(3-dimethylaminopropyl)-n-ethylcarbodiimide hydrochloride) and subsequently with TFA (trifluoroacetic acid).

Process variant e) describes the preparation of compounds of formulas I-5 or I-6. A compound of formula VI, for example 4-chloromethyl-benzoic acid (3S,4S)-4-[2-(4-benzyl-3-hydroxy-piperidin-1-yl)-ethanesulfonyl]-phenyl ester is treated with morpholine or 4-methyl-piperazin in a solvent, such as methylene chloride.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–3 describe the processes for preparation of the prodrugs of formula I in more detail. The starting compound of formula II (parent compound) may be prepared in accordance with schemes 4 to 6. The compounds, described in these schemes, are known compounds or may be prepared by known methods, for example in accordance with methods, described in WO 00/75109.

In the schemes the following abbreviations have been used:

| | |
|---|---|
| DAPEC | N-(3-dimethylaminopropyl)]-n-ethylcarbodiimide hydrochloride |
| DMAP | 4-dimethylaminopyridine |
| TFA | trifluoroacetic acid |

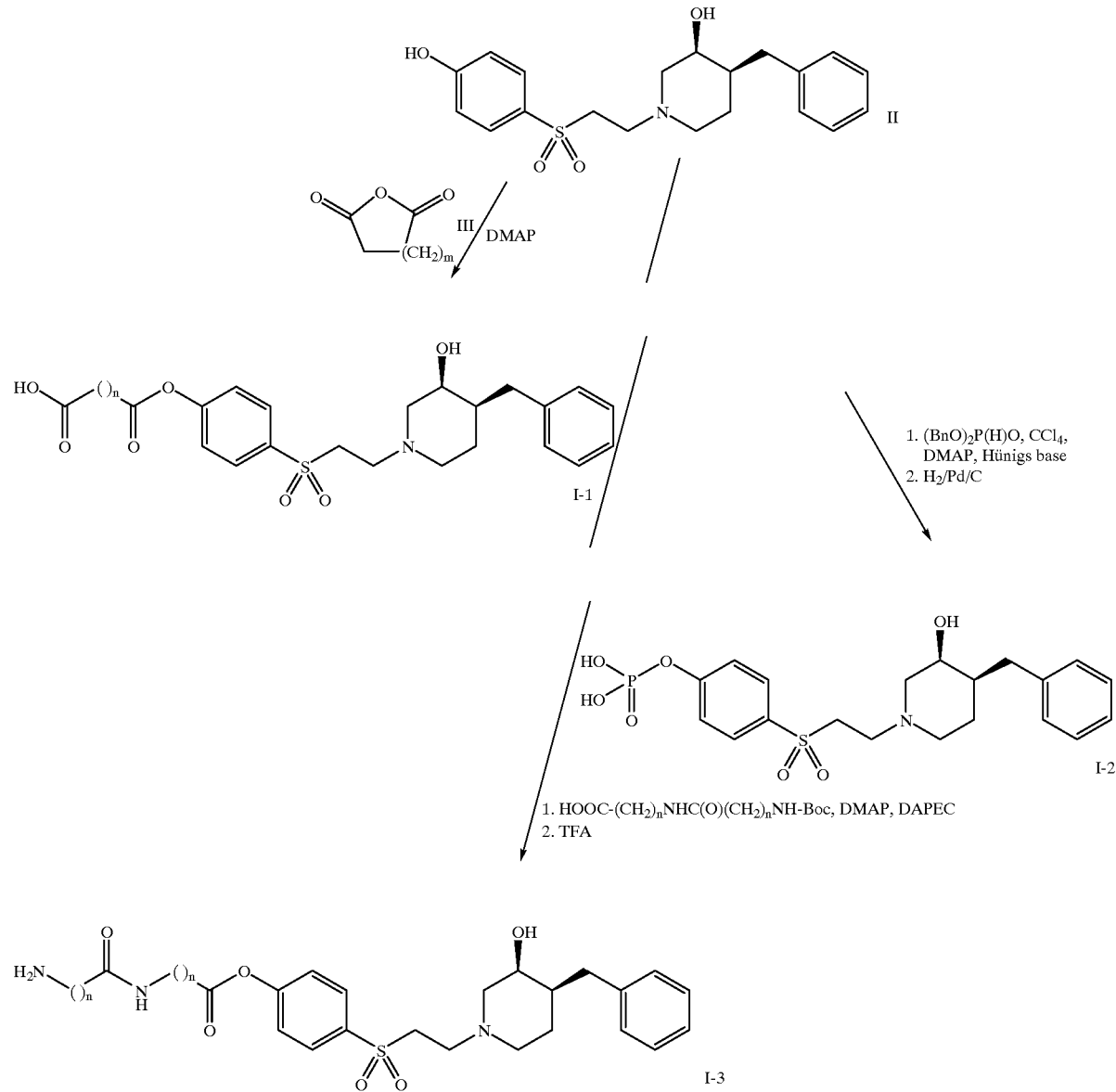

n is 2 to 4 and m is 1 to 3

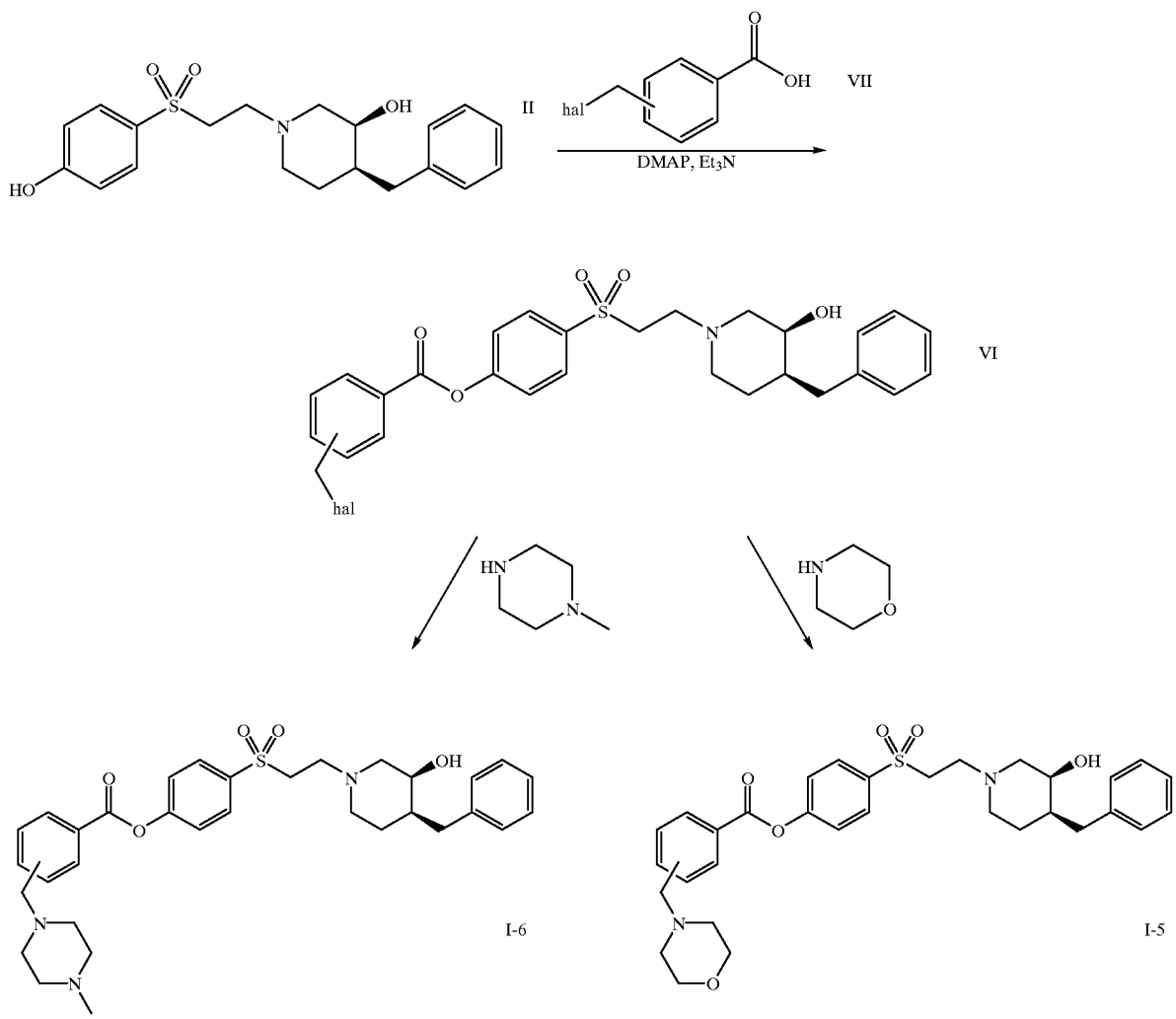
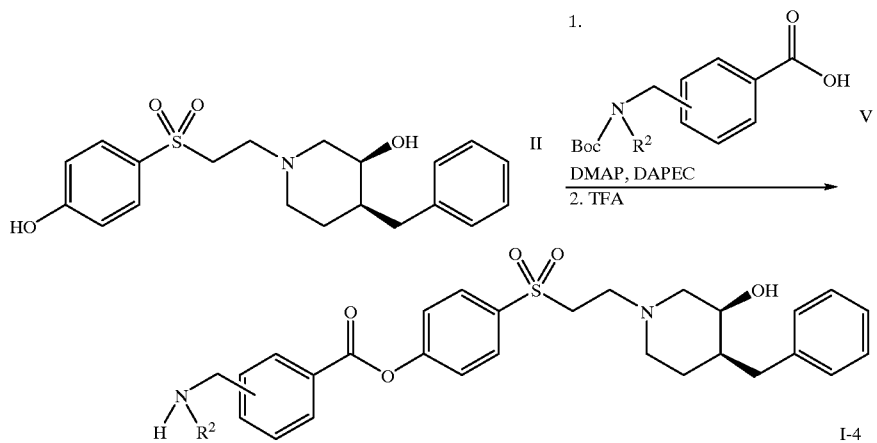
hal is halogen, such as chloro or bromo

Scheme 4
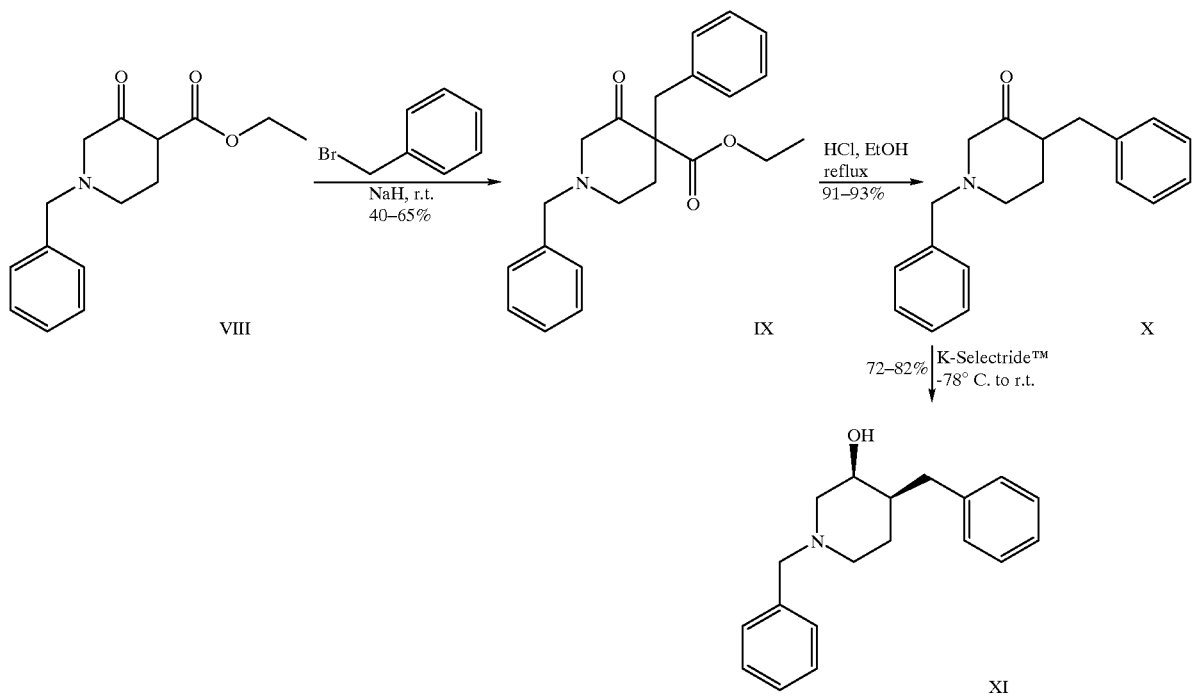
Scheme 5
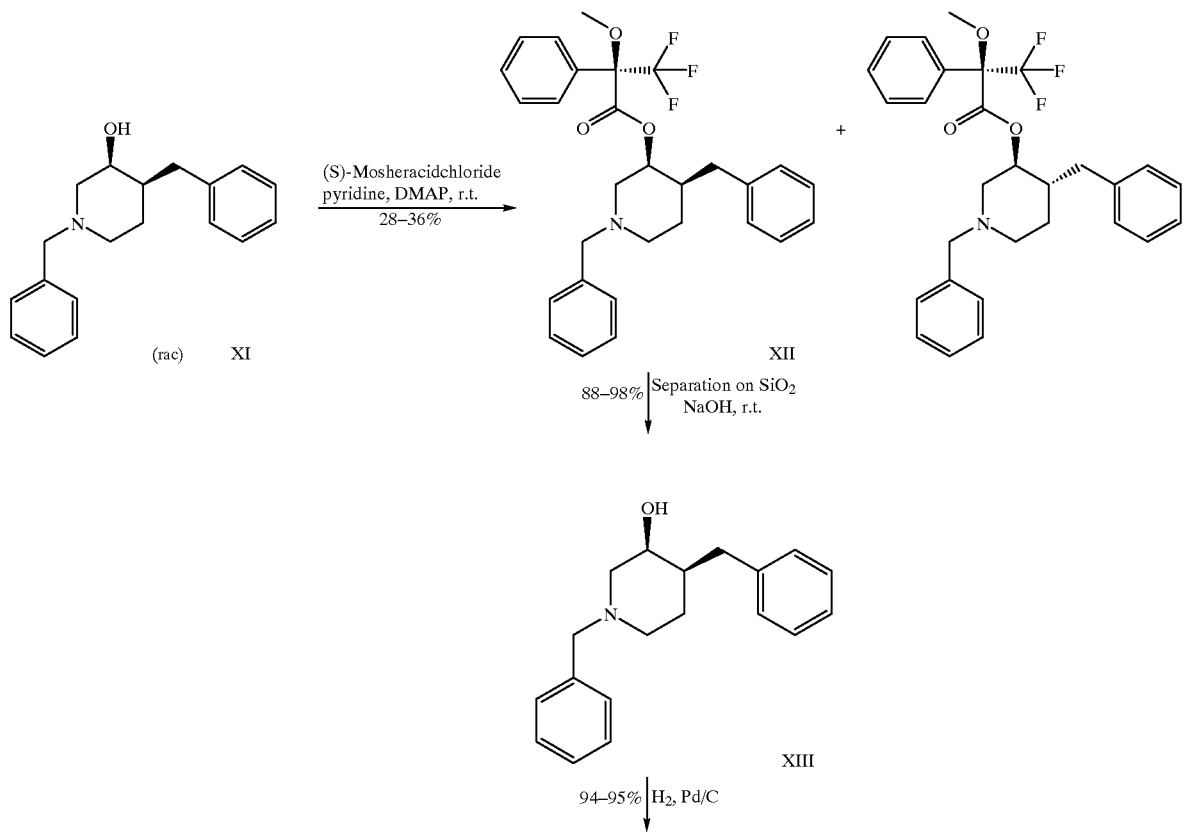

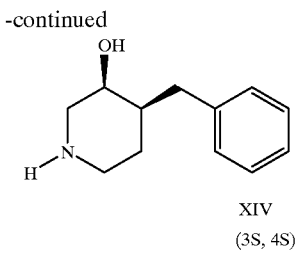

XIV
(3S, 4S)

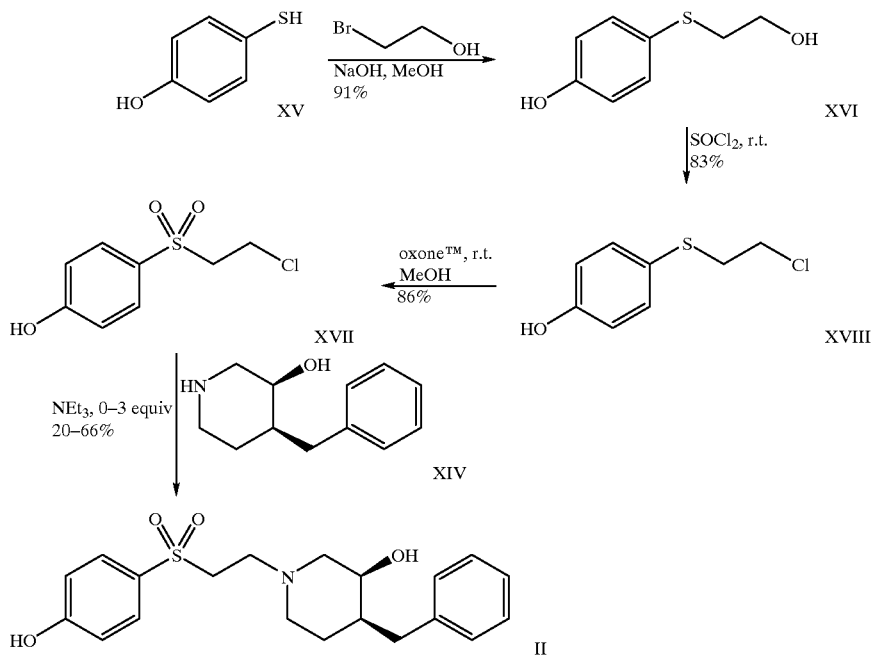

As mentioned above, the compounds of formula I and their pharmaceutically acceptable addition salts may be used as prodrlgs of the parent compounds of formula II, which possess valuable pharmacological properties.

All of the compounds of the present invention were investigated in accordance with the test given hereinafter. The evidence, that the inventive compounds of formula I may be used as prodrugs of their parent compounds of formula II is shown in accordance with the description given hereinafter.

The conversion of prodrugs to the corresponding parent compounds is due to a hydrolytic mechanism. There is well known evidence from the literature that similar reactions occur in vivo, hence the decision to study both the stability in plasma and blood was taken.

TEST DESCRIPTION

Plasma and blood samples from various species were spiked with equimolar amounts (26.7 μM) of the prodrug of the invention and parent drug in DMSO and incubated for different time intervals (up to 120 min) at 37° C. The reaction was stopped by protein precipitation with perchloric acid (0.5 M) followed by centrifugation (5 min. at 15,000 g). This procedure was found to be reliable enough at least when the drug analysis was performed immediately after the incubation.

The concentrations of formed parent drug in the supernatant was determined by LC-MS: The parent compound together with its hexa-$^{13}$C-labelled internal standard was enriched on a standard bore trapping column (Lichrospher100, RP18, 5 μm, 4×4 mm, Merck) and separated under isocratic conditions on a narrow-bore analytical column (Symmetry Shield, RP8, 3.5 μm, 2.1×50 mm Waters) by a mixture of formic acid and methanol as mobile phase. The whole effluent (200 μl/min) of the analytical column was passed to the turbo ion spray interface without splitting. Selected ion monitoring (SIM) in negative mode was used for single quadrupole mass spectrometric detection. The results were expressed as % converted to the parent compound, using the data of the parent drug as 100%-value.

In the following table the results of the above mentioned test are described.

| Compound of Example No. | Solubility (μg/ml at pH 7) | Solubility (μg/ml at pH 4) | Stability (2 hours) rat plasma | Stability (2 hours) human plasma |
|---|---|---|---|---|
| 1 | 7689 | 1800 | <10% | 10% |
| 2 | >37600 | 594 | 41% | 35% |

| Compound of Example No. | Solubility (μg/ml at pH 7) | Solubility (μg/ml at pH 4) | Stability (2 hours) rat plasma | Stability (2 hours) human plasma |
|---|---|---|---|---|
| 6 | 89 | 8500 | | |
| 7 | | 6706 | 98% | 91% |
| 9 | | 86600 | 100% | 100% |
| 10 | | 26100 | 100% | 100% |
| Compound of formula II (parent compound) | 47 | 7750 (pH 4.8) | | |

The results show that the prodrug approach of the present invention increases the solubility at pH 7.4 (physiological pH) compared with the parent compound (compound of formula II) thereby substantially reducing any precipitation in plasma and local intolerance at the injection site. An increase in solubility at physiological pH has been clearly reached for compound 1 and 2 and to a lesser extent for compound 6. The compounds 7, 9 and 10 were unstable at pH 7.4 over 24 hours, therefore their solubility could only be measured at pH 4.0. These data suggest a higher solubility at pH 7.4 for compounds 9 and 10 than for the parent compound. The solubility of compound 7 at pH 4.0 is similar to the parent compound, but due to the additional charge at pH 7.4 (calculated pKa for the benzylic amine 8.96), a higher solubility can be assumed at this pH.

The term "stability (2 hours) rat or human plasma" of 100% means that the prodrug of the invention in the plasma has been converted after 2 hours completely into the parent compound. In accordance with the test the inventive compounds of formula I are useful as prodrugs of their parent compounds of formula II.

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically acceptable acid addition salts can be processed with pharmaceutically inert, inorganic or organic excipients for the production of tablets, coated tablets, dragées and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples 1 to 17 illustrate the present invention without limiting it. All temperatures are given in degrees Celsius.

The preparation of compounds of formula I, starting with compounds of formula II, is described generically in the description in process variants a) to e) and in schemes 1 to 3. Specifically, the preparation of prodrugs is described in more detail in examples 1 to 10. Examples 11 to 17 describe the preparation of intermediates.

EXAMPLE 1

Succinic Acid Mono-{(3S,4S)-4-[2-(4-benzyl-3-hydroxy-piperidin-1-yl)-ethanesulfonyl]-phenyl}ester To a solution of 1.0 g (2.66 mmol) (3S,4S)-4-[2-(4-benzyl-3-hydroxy-piperidin-1-yl)-ethanesulfonyl]-phenol in 25 ml $CH_2Cl_2$ were added 320 mg (3.2 mmol) succinic acid and 390 mg (3.2 mmol) dimethylaminopyridine and the reaction mixture was refluxed for 20 hours. The reaction mixture was concentrated to 10 ml and was purified by chromatography over silica gel to give 100 mg (0.21 mmol, 7.4%) succinic acid mono-{(3S,4S)-4-[2-(4-benzyl-3-hydroxy-piperidin-1-yl)-ethanesulfonyl]-phenyl} ester as colorless oil.

MS: m/e=476.2 $(M+H^+)$.

EXAMPLE 2

Phosphoric Acid Mono-{(3S,4S)-4-[2-(4-benzyl-3-hydroxy-piperidin-1-yl)-ethanesulfonyl]-phenyl}ester A solution of 1.20 g, (1.73 mmol) phosphoric acid dibenzyl ester (3S,4S)-4-[2-(4-benzyl-3-hydroxy-piperidin-1-yl)-ethanesulfonyl]-phenyl ester in 40 ml MeOH and 6 ml water was hydrogenated at room temperature (20 bar, 5 h). The reaction mixture was concentrated to 20 ml and 500 ml water were added. The reaction mixture was filtered and the catalyst was washed with water. The filtrate was concentrated under reduced pressure until the product precipitates. The mixture was then cooled to 0° C. and 200 ml MeOH were added dropwise. After two hours the solid was filtered, washed with cold MeOH and dried at 60° C. under high vacuum to give 380 mg (0.83 mmol, 48%) of phosphoric acid mono-{(3S,4S)-4-[2-(4-benzyl-3-hydroxy-piperidin-1-yl)-ethanesulfonyl]-phenyl} ester as colorless crystalls.

MS: m/e=454.4 $(M-H)^-$.

EXAMPLE 3

4-Morpholin-4-ylmethyl-benzoic Acid (3S,4S)-4-[2-(4-benzyl-3-hydroxy-piperidin-1-yl)-ethanesulfonyl]-phenyl Ester To a solution of 200 mg (0.38 mmol) 4-chloromethyl-benzoic acid-(3S,4S)-4-[2-(4-benzyl-3-hydroxy-piperidin-1-yl)-ethanesulfonyl]-phenyl ester in 10 ml $CH_2Cl_2$ were added 53 □l (0.38 mmol) $Et_3N$ and 33 μl (0.38 mmol) morpholine. After 16 hours the reaction mixture was purified by chromatography over silica gel to give 70 mg (0.12 mmol, 32%) 4-morpholin-4-ylmethyl-benzoic acid (3S,4S)-4-[2-(4-benzyl-3-hydroxy-piperidin-1-yl)-ethanesulfonyl]-phenyl ester as a colorless solid.

MS: m/e=579.1 (M+H$^+$).

Following the general procedure of example 3 the compounds of example 4 to example 6 were prepared.

EXAMPLE 4

4-(4-Methyl-piperazin-1-ylmethyl)-benzoic Acid (3S,4S)-4-[2-(4-benzyl-3-hydroxy-piperidin-1-yl)-ethanesulfonyl]-phenyl Ester The title compound was prepared from 4-chloromethyl-benzoic acid (3S,4S)-4-[2-(4-benzyl-3-hydroxy-piperidin-1-yl)-ethanesulfonyl]-phenyl ester and 4-methylpiperazin in 27% yield as a colorless oil.

MS: m/e=592.2 (M+H$^+$).

EXAMPLE 5

3-(4-Methyl-piperazin-1-ylmethyl)-benzoic Acid (3S,4S)-4-[2-(4-benzyl-3-hydroxy-piperidin-1-yl)-ethanesulfonyl]-phenylester; Hydrochloride(1:3)

The title compound was prepared from 3-chloromethyl-benzoic acid (3S,4S)-4-[2-(4-benzyl-3-hydroxy-piperidin-1-yl)-ethanesulfonyl]-phenyl ester and 4-methylpiperazin, followed by the addition of HCl in 80% yield as a colorless solid.

MS: m/e=592.2 (M+H$^+$).

EXAMPLE 6

3-Morpholin-4-ylmethyl-benzoic Acid (3S,4S)-4-[2-(4-benzyl-3-hydroxy-piperidin-1-yl)-ethanesulfonyl]-phenyl Ester; Hydrochloride(1:2)

The title compound was prepared from 3-chloromethyl-benzoic acid (3S,4S)-4-[2-(4-benzyl-3-hydroxy-piperidin-1-yl)-ethanesulfonyl]-phenyl ester and morpholine, followed by the addition of HCl in 18% yield as a colorless solid.

MS: m/e=579.1 (M+H$^+$).

EXAMPLE 7

4-Aminomethyl-benzoic Acid (3S,4S)-4-[2-(4-benzyl-3-hydroxy-piperidin-1-yl)-ethanesulfonyl]-phenyl Ester; Hydrochloride(1:2)

A solution of 200 mg 4-(tert-butoxycarbonylamino-methyl)-benzoic acid (3S,4S)-4-[2-(4-benzyl-3-hydroxy-piperidin-1-yl)-ethanesulfonyl]-phenyl ester in 3.8 ml TFA was stirred for 1 hour at 0° C. The solvent was removed under reduced pressure and the crude product was diluted in diethylether and 3 drops of a saturated HCl-solution in diethylether were added. Filtration yielded 120 mg (0.22 mmol, 67%) 4-aminomethyl-benzoic acid (3S,4S)-4-[2-(4-benzyl-3-hydroxy-piperidin-1-yl)-ethanesulfonyl]-phenyl ester; hydrochloride(1:2) as colorless crystalls.

MS: m/e=509.4 (M+H$^+$).

Following the general procedure of example 7 the compounds of example 8 to example 10 were prepared.

EXAMPLE 8

3-(3-Amino-propionylamino)-propionic Acid (3S,4S)-4-[2-(4-benzyl-3-hydroxy-piperidin-1yl)-ethanesulfonyl]-phenyl Ester; 1:1 HCl The title compound was prepared from 3-(3-tert-butoxycarbonylamino-propionylamnino)-propionic acid (3S,4S)-4-[2-(4-benzyl-3-hydroxy-piperidin-1-yl)-ethanesulfonyl]-phenyl ester in 13% yield as a colorless solid.

MS: m/e=518.2 (M+H$^+$).

EXAMPLE 9

3-Methylaminomethyl-benzoic Acid (3S,4S)-4-[2-(4-benzyl-3-hydroxy-piperidin-1-yl)-ethanesulfonyl]-phenyl Ester Hydrochloride (1:2)

The title compound was prepared from 3-(3-tert-butoxycarbonyl-methyl-amino-methyl) benzoic acid and (3S,4S)-4-[2-(4-benzyl-3-hydroxy-piperidin-1-yl)-ethanesulfonyl]-phenyl ester in 93% yield as a colorless solid.

MS: m/e=523.2 (M+H$^+$).

EXAMPLE 10

4-Methylaminomethyl-benzoic Acid (3S,4S)-4-[2-(4-benzyl-3-hydroxy-piperidin-1-yl)-ethanesulfonyl]-phenyl Ester Hydrochloride (1:2)

The title compound was prepared from 4-(tert-butoxycarbony-methyl-lamino-methyl)-benzoic acid (3S,4S)-4-[2-(4-benzyl-3-hydroxy-piperidin-1-yl)-ethanesulfonyl]-phenyl ester in 94% yield as a colorless solid.

MS: m/e=523.2 (M+H$^+$).

EXAMPLE 11

Phosphoric Acid Dibenzyl Ester (3S,4S)-4-[2-(4-benzyl-3-hydroxy-piperidin-1-yl)-ethanesulfonyl]-phenyl Ester To a solution of 500 mg (133 mmol) (3S,4S)-4-[2-(4-benzyl-3-hydroxy-piperidin-1-yl)-ethanesulfonyl]-phenol in 20 ml acetonitrile were added 0.64 ml (6.7 mmol) CCl$_4$, 16.3 mg (0.13 mmol) DMAP and 0.48 ml (2.9 mmol) N,N-diisopropylethylamine. The reaction mixture was stirred for 15 min at room temperature and 0.43 ml (1.9 mnmol) dibenzylphosphite were added dropwise. After 20 min. 20 ml sat. NaHCO$_3$ solution was added and the aqueous phase was extracted with ethylacetate (3×30 ml) and the combined organic layers were washed with water, dried over MgSO$_4$, filtrated and the solvent was removed under reduced pressure. Purification of the crude product by chromatography over silica gel (ethylacetate/hexane 2/1) yielded 700 mg (11 mmol, 83%) phosphoric acid dibenzyl ester (3S,4S)-4-[2-(4-benzyl-3-hydroxy-piperidin-1-yl)-ethanesulfonyl]-phenyl ester as a colorless solid.

MS: m/e=635.7 (M+H$^+$).

EXAMPLE 12

4-(tert-Butoxycarbonylamino-methyl)-benzoic Acid (3S,4S)-4-[2-(4-benzyl-3-hydroxy-piperidin-1-yl)-ethanesulfonyl]-phenyl Ester To a solution of 500 mg (1.33 mmol) (3S,4S)-4-[2-(4-benzyl-3-hydroxy-piperidin-1-yl)-ethanesulfonyl]-phenol in 10 ml methylenechloride were added 368 mg (1.46 mmol) 4-(tert-butoxycarbonylamino-methyl)-benzoic acid, 16.3 mg (0.133 mmol) DMAP und 511 mg (2.66 mmol) N-(3-dimethylaminopropyl)-N-ethylcarbodiimide hydrochloride and the reaction mixture was stirred at 0° C. After 1 hour, 0.5 N HCl was added and the aqueous layer was extracted with methylenechloride. The combined organic layers were washed with 0.5N HCl solution and brine, dried over NaSO$_4$, filtered and the solvent was removed under reduced pressure to give the crude product. Crystallization from diethylether yielded 280 mg (0.460 mmol, 35%) 4-(tert-butoxycarbonylamino-methyl)-benzoic acid (3S,4S)-4-[2-(4-benzyl-3-hydroxy-piperidin-1-yl)-ethanesulfonyl]-phenyl ester as colorless crystalls.

MS: m/e=609.4 (M+H$^+$).

Following the general procedure of example 12 the compounds of example 13 to example 15 were prepared.

EXAMPLE 13

3-(3-tert-Butoxycarbonylamino-propionylamino)-propionic Acid (3S,4S)-4-[2-(4-benzyl-3-hydroxy-piperidin-1-yl)-ethanesulfonyl]-phenyl Ester The title compound was prepared from (3S,4S)-4-[2-(4-benzyl-3-hydroxy-piperidin-1-yl)-ethanesulfonyl]-phenol and 3-(3-tert-butoxycarbonylamino-propionylamino)-propionic acid in 13% yield as a colorless solid.

MS: m/e=618.2 (M+H$^+$).

EXAMPLE 14

3-[(tert-Butoxycarbonyl-methyl-amino)-methyl]-benzoic Acid (3S,4S)-4-[2-(4-benzyl-3-hydroxy-piperidin-1-yl)-ethanesulfonyl]-phenyl Ester The title compound was prepared from (3S,4S)-4-[2-(4-benzyl-3-hydroxy-piperidin-1-yl)-ethanesulfonyl]-phenol and 3-[(tert-butoxycarbonyl-methyl-amino)-methyl]-benzoic acid in 70% yield as a colorless gum.

MS: m/e=623.2 (M+H$^+$).

EXAMPLE 15

4-[(tert-Butoxycarbonyl-methyl-amino)-methyl]-benzoic Acid (3S,4S)-4-[2-(4-benzyl-3-hydroxy-piperidin-1-yl)-ethanesulfonyl]-phenyl Ester The title compound was prepared from (3S,4S)-4-[2-(4-benzyl-3-hydroxy-piperidin-1-yl)-ethanesulfonyl]-phenol and 4-[(tert-butoxycarbonyl-methyl-amino)-methyl]-benzoic acid in 99% yield as a light brown oil.

MS: m/e=623.2 (M+H$^+$).

EXAMPLE 16

4-Chloromethyl-benzoic Acid (3S,4S)-4-[2-(4-benzyl-3-hydroxy-piperidin-1-yl)-ethanesulfonyl]-phenyl Ester To a solution of 500 mg (1.33 mmol) (3S,4S)-4-[2-(4-benzyl-3-hydroxy-piperidin-1-yl)-ethanesulfonyl]-phenol in 10 ml CH$_2$Cl$_2$ were added 20 mg (0.16 mmol) DMAP and 162 mg (1.60 mmol) Et$_3$N and 302 mg (1.60 mmol) 4-chlormethylbenzoylchloride. After 1 hour water was added and the aequous phase was extracted with methylenechloride (3×20 ml). The combined organic layers were dried over MgSO$_4$, filtered and the solvent was removed under reduced pressure. The crude product was purified by chromatography over silica gel to give 280 mg (0.53 mmol, 40%) 4-chloromethyl-benzoic acid 4-[2-(4-benzyl-3-hydroxy-piperidin-1-yl)-ethanesulfonyl]-phenyl ester as colorless foam.

MS: m/e=528.2 (M).

Following the general procedure of example 16 the compound of example 17 was prepared.

EXAMPLE 17

3-Chloromethyl-benzoic Acid (3S,4S)-4-[2-(4-benzyl-3-hydroxy-piperidin-1-yl)-ethanesulfonyl]-phenyl Ester The title compound was prepared from (3S,4S)-4-[2-(4-benzyl-3-hydroxy-piperidin-1-yl)-ethanesulfonyl]-phenol and 3-chlormethylbenzoylchloride in 80% yield as a colorless solid.

MS: m/e=528.1 (M).

EXAMPLE A

Tablets of the following composition are manufactured in the usual manner:

| mg/tablet | |
| --- | --- |
| Prodrug | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| mg/capsule | |
| --- | --- |
| Prodrug | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

| mg/supp. | |
| --- | --- |
| Prodrug | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula

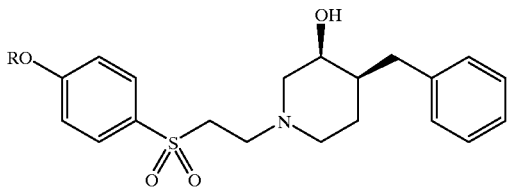

wherein
R is
 a) —C(O)(CH$_2$)$_n$C(O)OH,
 b)

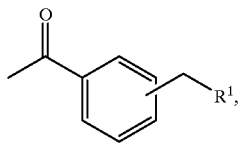

wherein R$^1$ is —N(R$^2$)(R$^3$) or a five or six member aromatic or non-aromatic heterocyclic ring containing one or more heteroatoms selected from nitrogen, oxygen or sulfur, said ring being unsubstituted or substituted by lower alkyl,
 c) —P(O)(OH)$_2$, or is
 d) —C(O)(CH$_2$)$_n$NHC(O)(CH$_2$)$_n$N(R$^2$)(R$^3$);
R$^2$/R3 are hydrogen or lower alkyl; and
n is 1, 2, 3 or 4; or a pharmaceutically acceptable acid addition salt thereof.

2. A compound of formula I of claim 1, wherein R is —C(O)(CH$_2$)$_n$C(O)OH.

3. A compound of claim 2, which is succinic acid mono-{(3S,4S)-4-[2-(4-benzyl-3-hydroxy-piperidin-1-yl)-ethanesulfonyl]-phenyl}ester.

4. A compound of formula I of claim 1, wherein R is

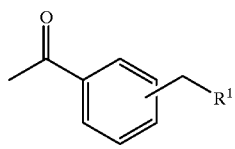

and R$^1$ is as in claim 1.

5. A compound of claim 4, wherein R$^1$ is morpholinyl.

6. A compound of claim 5 wherein the compound is 4-morpholin-4-yl-methyl-benzoic acid (3S,4S)-4-[2-(4-benzyl-3-hydroxy-piperidin-1-yl)-ethanesulfonyl]-phenyl ester.

7. A compound of claim 5, wherein the compound is 3-morpholin-4-ylmethyl-benzoic acid (3S,4S)-4-[2-(4-benzyl-3-hydroxy-piperidin-1-yl)-ethanesulfonyl]-phenyl ester.

8. A compound of claim 4 wherein R$^1$ is 4-methyl-piperazinyl.

9. The compound of claim 8, wherein the compound is 4-(4-methyl-piperazin-1-ylmethyl)-benzoic acid (3S,4S)-4-[2-(4-benzyl-3-hydroxy-piperidin-1-yl)-ethanesulfonyl]-phenyl ester.

10. A compound of claim 8, wherein the compound is 3-(4-methyl-piperazin-1-ylmethyl)-benzoic acid (3S,4S)-4-[2-(4-benzyl-3-hydroxy-piperidin-1-yl)-ethanesulfonyl]-phenylester.

11. A compound of claim 4 wherein R$^1$ is —N(R$^2$)(R$^3$), wherein R$^2$ and R$^3$ are as in claim 1.

12. A compound of claim 11, wherein the compound is 4-aminomethyl-benzoic acid (3S,4S)-4-[2-(4-benzyl-3-hydroxy-piperidin-1-yl)-ethanesulfonyl]-phenyl ester.

13. A compound of claim 11, wherein the compound is 3-methylaminomethyl-benzoic acid (3S,4S)-4-[2-(4-benzyl-3-hydroxy-piperidin-1-yl)-ethanesulfonyl]-phenyl ester.

14. A compound of claim 11, wherein the compound is 4-methylaminomethyl-benzoic acid (3S,4S)-4-[2-(4-benzyl-3-hydroxy-piperidin-1-yl)-ethanesulfonyl]-phenyl ester.

15. A compound of formula I of claim 1, wherein R is —P(O)(OH)$_2$.

16. A compound of claim 15, wherein the compound is phosphoric acid mono-{(3S,4S)-4-[2-(4-benzyl-3-hydroxy-piperidin-1-yl)-ethanesulfonyl]-phenyl}ester.

17. A compound of formula I of claim 1, wherein R is —C(O)(CH$_2$)$_2$NHC(O)(CH$_2$)$_2$NH$_2$.

18. A compound of claim 17, wherein the compound is 3-(3-amino-propionylamino)-propionic acid (3S,4S)-4-[2-(4-benzyl-3-hydroxy-piperidin-1-yl)-ethanesulfonyl]-phenyl ester.

* * * * *

UNITED STATES PATENT AND TRADEMARK OFFICE
CERTIFICATE OF CORRECTION

PATENT NO. : 6,407,235 B1
DATED : June 18, 2002
INVENTOR(S) : Alexander Alanine et al.

It is certified that error appears in the above-identified patent and that said Letters Patent is hereby corrected as shown below:

Column 3,
Line 4, the second option for the substituent "R" (i.e. the structure) reads:

"wherein
 R is
 a) $-C(O)(CH_2)_nC(O)OH$,

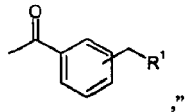
,"

The structure should be preceded by "b)" as follows:

— wherein
 R is
 a) $-C(O)(CH_2)_nC(O)OH$, b) 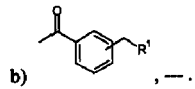 , — .

Column 6,
Lines 36, 41, 55 and 66, which begin with "reacting" or "cleaving" read as follows:

"reacting a compound of formula II with a compound of formula $$HOOC-(CH_2)_nNHC(O)(CH_2)_nNH\text{-}Boc \quad IV,$$

cleaving off the Boc group to give a compound of formula

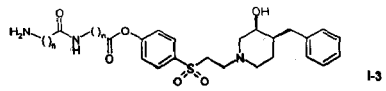
I-3 reacting a compound of formula II with a compound of formula

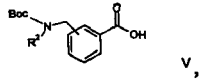
V, cleaving off the Boc group with TFA (trifluoroacetic acid) to give a compound of formula

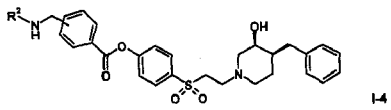
I-4 reacting a compound of formula".

UNITED STATES PATENT AND TRADEMARK OFFICE
CERTIFICATE OF CORRECTION

PATENT NO. : 6,407,235 B1
DATED : June 18, 2002
INVENTOR(S) : Alexander Alanine et al.

It is certified that error appears in the above-identified patent and that said Letters Patent is hereby corrected as shown below:

Scheme 3 should read as follows:

--

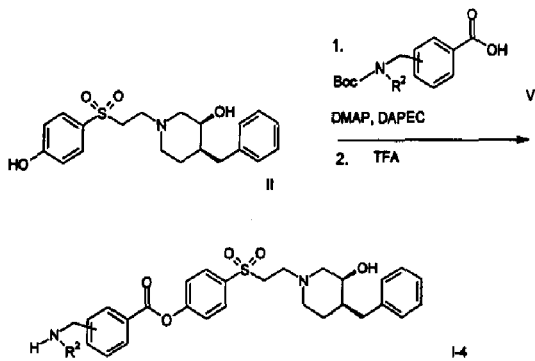

$R^2$ is hydrogen or lower alkyl. --

Signed and Sealed this

Twenty-eighth Day of December, 2004

JON W. DUDAS
*Director of the United States Patent and Trademark Office*